United States Patent [19]

Santos

[11] Patent Number: 4,648,402

[45] Date of Patent: Mar. 10, 1987

[54] BLOOD VESSEL DILATING SURGICAL INSTRUMENT

[76] Inventor: Manuel V. Santos, 126 Pulaski St., Newark, N.J. 07105

[21] Appl. No.: 783,652

[22] Filed: Oct. 3, 1985

[51] Int. Cl.$^4$ .................. A61B 17/22; A61M 29/00
[52] U.S. Cl. .................................................. 128/345
[58] Field of Search ........ 128/304, 305, 328, 341–345, 128/751, 756; 604/104–109

[56] References Cited

U.S. PATENT DOCUMENTS

| | | | |
|---|---|---|---|
| 1,677,671 | 7/1928 | Councill | 128/328 |
| 3,147,749 | 9/1964 | Marsh | 128/305 |
| 4,281,658 | 8/1981 | Child | 128/341 |
| 4,320,762 | 3/1982 | Bentov | 128/345 |
| 4,467,790 | 8/1984 | Schiff | 128/344 |
| 4,574,800 | 3/1986 | Peers-Trevarton | 128/785 |

Primary Examiner—Carlton R. Croyle
Assistant Examiner—Jane E. Obee
Attorney, Agent, or Firm—R. Martin Oliveras

[57] ABSTRACT

A surgical instrument for dilating blood vessels comprises: a front multilinkage mechanism; an intermediate hollow cable-wire structure combination; and a rear manually operated control mechanism. The rear manually operated control mechanism further comprises: a rearmost thumb ring being connected to a stationary member; and index finger and ring finger rings being connected to a longitudinally movable member. Motion of the index finger and the ring finger rings relative to the thumb ring causes similar motion of a wire which is located in the hollow cable. The front multilinkage mechanism further comprises: a plurality of longitudinal ribs being located on a rear stationary section; a similar plurality of rear linkages; a similar plurality of front linkages; and a similar plurality of longitudinal ribs being located on a movable front section. The front end of the wire runs through the rear stationary section to the front stationary section and has attached thereto a spherical ball adjacent the rear linkages. The frontmost end of the wire inserts into and moves freely within the front stationary section. Rearward actuation of the index finger and ring finger rings relative to the thumb ring causes similar rearward motion of the wire thereby causing similar rearward motion of the sphere. The rear surface of the sphere then applies a force to the internal edges of the rear linkages thereby causing the multilinkage mechanism to open and expand. Forward actuation of the index and ring finger rings relative to the thumb ring causes similar forward motion of the wire thereby causing similar forward motion of the sphere. The rear surface of the sphere loses contact with the internal edges of the rear linkages thereby causing the multilinkage mechanism to collapse and close. In the closed configuration, the sphere is neatly contained within the internal concave edges of the rear linkages. Entry of the multilinkage mechanism into the tissue is enhanced by a convex front surface on the movable front section and by slanted front edges of on the front ribs; and exit out of the tissue is enhanced by convex rear edges on the rear stationary section and the slanted rear edges of the rear ribs. The front linkages and the stationary front section of the multilinking mechanism are displaced rearwardly in the open configuration and are displaced anteriorly in the closed configuration. A set screw located on the rear manually operated control mechanism allows for maintaining the front multilinkage mechanism in the open or closed configurations or any configuration therebetween.

7 Claims, 8 Drawing Figures

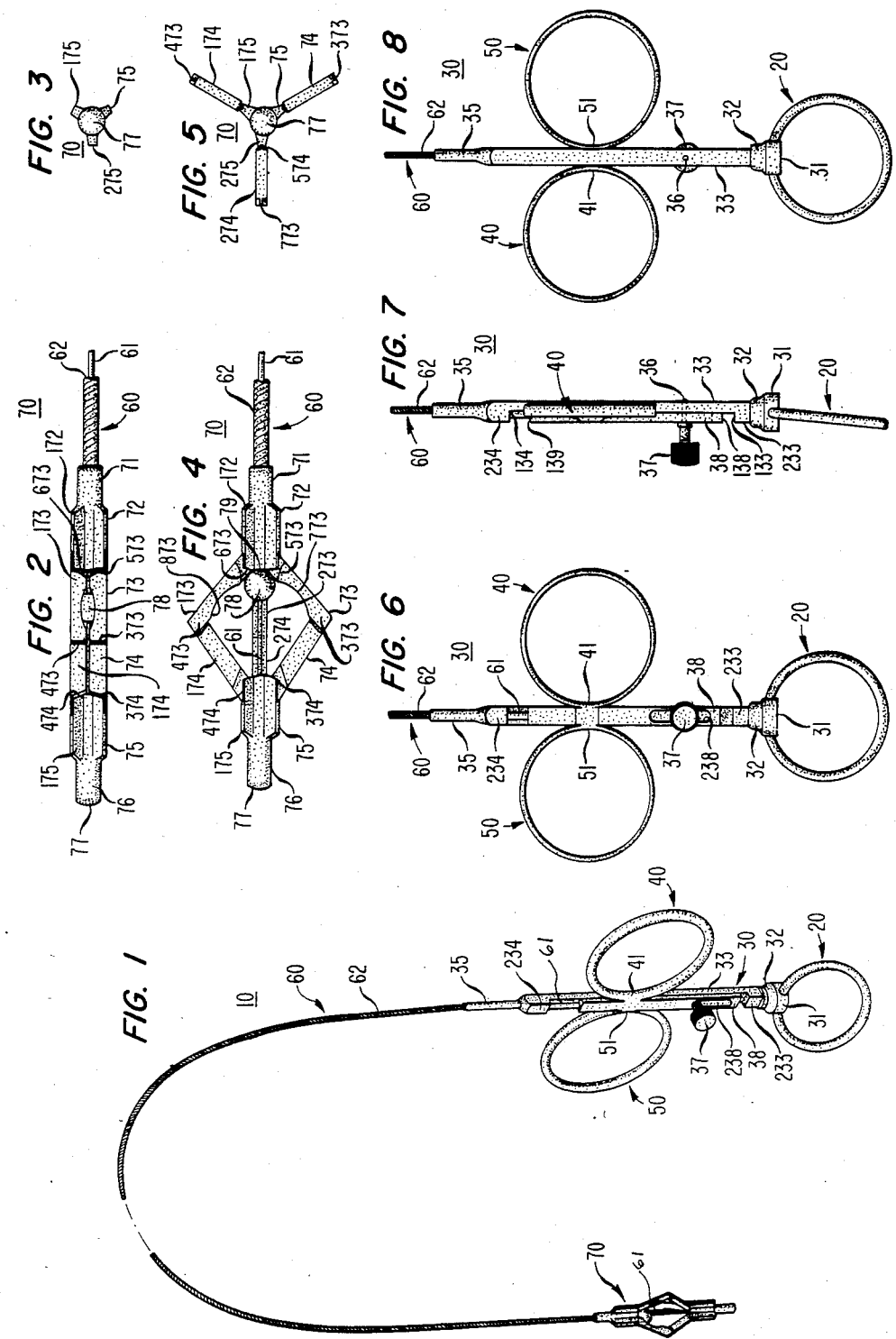

BLOOD VESSEL DILATING SURGICAL INSTRUMENT

FIELD OF THE INVENTION

This invention relates to surgical instruments and in particular to such instruments for dilating blood vessels or other luminal structures or ducts.

OTHER RELATED APPLICATIONS

This utility patent application is related to the prior design patent application by the same applicant herein having Ser. No. 680,558, filing date 12/11/84, and being entitled "Vein Marker".

DISCUSSION OF THE PRIOR ART

Several prior art patents reveal instruments for dilating blood vessels or the like as follows:

Richter U.S. Pat. No. 2,655,154 entitled "Valvulotome" discloses a valvulotome comprising an elongated tubular shank of non circular cross sectional shape, an elonagted tubular stem, an outwardly tapered cap, elongated blades, a shaft, arms, a tubular nut, nut engaging means, movement indicating means, and spring means. Specifically disclosed are nut 40, handle or shank 10, slot 50, graduating marks 51, screw 52, graduating mark 53, stem 11, slots 20 and 21, pivot pin 32, pivot pin 33, arms 26 and 27, blades 18 and 19, loop spring 31, cutting edges 34 and 35, cap 13, and pin 16;

Hoffman U.S. Pat. No. 2,816,552 entitled "Teat Bistoury With Improved Cutter Blade Adjusting Means" discloses a teat bistoury comprising a rigid barrel, a rod, a bladed expansible and contractible cutter unit, rod rotating means, and a rotatable finger grip. Specifically disclosed are stop shoulders 28 and 30, cylindrical finger grip 22, barrel 14, flat spring steel cutter blades 60, rod or shaft 40, cutter unit 52, ferrules 56 and 58, shoulder 54, screw 44, head 46, nose 48, and solder 50;

Fogarty U.S. Pat. No. 3,472,230 entitled "Umbrella Catheter" discloses an instrument comprising a flexible tube, a flexible control wire, a plurality of spring stays, a tip member, and an umbrella of flexible material. Specifically disclosed are handle fitting 13, flexible umbrella control wire 12, handle fitting 11, flexible plastic catheter tube 10, slide 15, spring wires 21, umbrella 30, tip 25, and umbrella frame 20;

Hines U.S. Pat. No. 3,517,128 entitled "Surgical Expanding Arm Dilator" discloses a surgical dilator comprising a guide rod, s shiftable cup shaped collar, and a skirt portion. Specifically disclosed are handle 12, set screw 17, radial flange 40, tubular sleeve 42, bowl portion 44, bead 30, split pivot ring 24, rod holders 22, expansion ribs 18, central axially extending guide rod 10, medial section 20, composite flexible expansion slots 26, and cup 34;

Van patten U.S. Pat. No. 3,557,794 entitled "Arterial Dilation Device" discloses a catheter comprising an elongated tubular device, an actuating wire, tubing, cylindrical ferrules, and a plurality of flexure beams. Specifically disclosed are enlarged member 18, apertured drum 19, catheter material 1, proximal fitting 2, metal ferrule 6, flexure beams 10, limiting tube 14, ferrule 11, member 12, actuator wire 5, and hemispherical end 13; and Evans U.S. Pat. No. 4,307,722 entitled "Dilators For Arterial Dilation" discloses a dilator comprising a longitudinally extending tubular member, and guide means. Specifically disclosed are annular member 20, end portion 16, spring wire guide 18, bipartite distal end portion 14, sack portion 26, enlarged distal end portion 24, dilator 10, support member 12, and tubular member 13.

The above cited prior art patents do not appear to reveal the structure and mechanism of the present invention.

Objects of the present invention are therefor to provide: a surgical instrument which is expansible and collapsible within a blood vessel and which is inserted into the operative site in the collapsed configuration and then expanded therein; a surgical instrument which has the expansible/collapsible structure at one end and which has the manually adjustable means at the other end; and a surgical instrument which includes means for indicating the extent of expansion of the members so that expansion to a predetermined amount can be effected.

SUMMARY OF THE PRESENT INVENTION

A summary and features of the present invention are that:

a. a surgical instrument for dilating blood vessels or the like comprises: a front multilinkage mechanism; an intermediate connecting hollow cable-wire structure combination; and a rear manually operated control mechanism;

b. the rear manually operated control mechanism further comprises: a rearmost stationary thumb ring being rotatably connected to a stationary member; movable index finger and ring finger rings being fixedly connected to a longitudinally movable member; and set screw means being threaded onto the stationary member for adjustably fixing the location of the movable member;

c. the hollow cable-wire structure combination further comprises: a hollow cable which is fixedly connected to the front end of the stationary member and to the rear end of the rear stationary section of the front multilinkage mechansim; and a wire which is fixedly connected to the front end of the movable member and to a sphere which is part of the multilinkage mechanism, a more anterior portion of the wire being freely inserted into and movable within the front movable section of the front multilinkage mechanism;

d. the front multilinkage mechanism further comprises: a rear stationary section to which the front end of the cable is fixedly connected including a plurality of longitudinal ribs and including a longitudinal central hole for accommodating the wire, each rear rib including a rear slanted edge; a similar plurality of rear linkages each including a concave inner edge and each being directed along the same longitudinal direction as their respective rear ribs; a similar plurality of front linkages each being directed along the same longitudinal direction as their respective rear linkages; and a movable front section including a similar plurality of ribs each being directed along the same longitudinal direction as their respective front linkages, each front rib further including a front slanted edge; and a sphere having the wire therethrough and being fixedly connected thereto such that the wire continues forward freely into a longitudinal central hole in the movable front section;

e. such that rearward motion of the movable rings relative to the stationary ring causes similar rearward motion of the wire whereby the rear surface of the sphere applies a force to the internal edges of the rear linkages up to the frontmost surface of the stationary rear section to cause unidirectional rotation in a first direction of the rear linkages relative to the stationary rear section, to cause unidrectional rotation in a second direction of the front linkages relative to the movable front section and rearward displacement of the front linkages, to cause relative rotation of the front end of the rear linkages and the rear ends of the front linkages, to cause free rearward displacement of the wire within the longitudinal central hole of the movable front section and to cause rearward displacement of the movable front section to expand and open the front multilinkage mechanism;

f. such that forward motion of the movable rings relative to the stationary ring causes similar forward motion of the wire whereby the rear surface of the sphere separates from the frontmost surface of the stationary rear section and the concave internal edges of the rear linkages to cause unidirectional rotation in the second direction of the rear linkages relative to the stationary rear section, to cause unidirectional rotation in the first direction of the front linkages relative to the movable front section and forward displacement of the front linkages, to cause forward displacement of the wire within the longitudinal central hole of the movable front section, to cause relative rotation of the front end of the rear linkages and the rear end of the front linkages, and to cause forward displacement of the movable front section such that the sphere is surrounded neatly by the internal concave edges of the rear linkages to collpase and close the front multilinkage mechanism; there being colinearity of each associated rear rib, rear linkage, front linkage, and front rib.

Advantages of the present invention are therefor that: the colinearity of the rear ribs, rear linkages, front linkages, and front ribs, and the slanted rear edges of the rear ribs and the slanted front edges of the front ribs provide a streamlined shape to allow easy entry into the exit from the tissue in the closed configuration; the rear manually operated control mechanism allows for manual opening and closing of the front multilinkage mechanism with one hand using the three rings while the specific configuration of the front multilinkage mechanism can de adjusted and fixed with the other hand using the set screw means; the instrument as a whole is simple and durable in construction; the instrument as a whole requires little radial space in the closed configuration to allow for easy entry into the tissue.

DESCRIPTION OF THE DRAWING

The above and other objects, features, and advantages of the present invention will be better appreciated from a reading of the following detailed description with reference to the drawing in which:

FIG. 1 is a perspective view of the Blood Vessel Dilating Surgical Instrument of the present invention in the open configuration;

FIG. 2 is a side view of the front multilinkage mechanism of the present invention in the closed configuration;

FIG. 2A is a partially cross sectional side view of the front hollow movable cylindrical section of the front multilinkage mechanism in the closed configuration;

FIG. 3 is a front view of the front multilinkage mechanism in the closed configuration;

FIG. 4 is a side view of the front multilinkage mechanism in the open configuration;

FIG. 4A is a partially cross sectional side view of the front hollow movable cylindrical section of the front multilinkage mechanism in the open configuration;

FIG. 5 is a front view of the front multilinkage mechanism in the open configuration;

FIG. 6 is a top view of the rear manually operated control mechansim of the present invention;

FIG. 7 is a side view of the rear manually operated control mechanism; and

FIG. 8 is a bottom view of the rear manually operated control mechanism.

DETAILED DESCRIPTION

FIG. 1 is a perspective view of Blood Vessel Dilating Surgical Instrument 10 of the present invention in the open configuration. Instrument 10 comprises: thumb ring 20; rear manually operated control mechanism 30; finger ring 40; finger ring 50; intermediate hollow cable-wire structure combination 60; and front multilinkage mechanism 70 in the open configuration. Ring 20 is rotatably connected to mechanism 30 at rear end section 31 while rings 40 and 50 are fixedly connected to mechanism 30 at locations 41 and 51, respectively. Anterior to rear end section 31 is tapered intermediate section 32 being fixedly connected thereto. Anterior to section 32 is longitudinal section 33 being fixedly connected thereto. Finally, anterior to section 33 is tapered hollow cylindrical longitudinal section 35 including a longitudinal central hole and being fixedly connected thereto. Mechanism 30 further comprises longitudinally slidable member 38 including longitudinal slot 238 and having rings 40 and 50 fixedly connected thereto at locations 41 and 51, respectively. Rotatably connected to section 33 by means of a threaded member is set screw means 37 for adjustably fixing the longitudinal location of member 38 relative to member 33. The rear end of member 33 includes an expanded portion 233 while the front end of member 33 includes an expanded portion 234 further including a longitudinal central hole therethrough. Accordingly, member 38 slides in a longitudinal direction along and adjacent to the narrower intermediate portion of member 33 and has its motion limited in the rearward direction by the front end of slot 238 and has its motion limited in the forward direction by the front end of slot 238. In operation, the operator's thumb fits into ring 20, his right index finger fits into ring 40, and his right ring finger fits into ring 50, with the palm of the hand being adjacent the underside of member 33, such that the motion of the ring finger and the index finger toward and away from the thumb causes motion of member 38 relative to member 33. Anterior to member 35 is interconnecting hollow cable-wire structure combination 60, cable 62 thereof being fixedly connected to member 35 and wire 61 being slidable within cable 62 in response to the motion of member 38. The front end of structure 60 is connected to mechanism 70. Also shown is part of flexible longitudinally directed wire 61 having its rearmost end being fixedly attached to the anteriormost surface of member 38, such wire 61 also being inserted into a longitudinal central hole being located on portion 234.

FIG. 2 is a side view of front multilinkage mechanism 70 of the present invention in the closed configuration. Mechanism 70 further comprises: rear hollow stationary cylindrical section 71 including a longitudinal central hole and being fixedly connected to the front end of cable 62 which is part of cable structure 60; longitudinal rear ribs 72 and 172 being part of stationary rear section 71; rear linkages 73 and 173; internal ball or sphere 78 being fixedly connected to this front extension of wire 61; front linkages 74 and 174; front hollow cylindrical section 76 including a longitudinal central hole; longitudinal front ribs 75 and 175 being a part of movable front section 76; and front concave surface 77 of section 76. Rear ribs 72 and 172 are slanted at their rear ends to allow extraction of member 70 in the closed configuration from the blood vessel while front ribs 75 and 175 are slanted at their front ends to allow insertion of mechanism 70 in the closed configuration into the blood vessel. The outer edges of rear rib 72, rear linkage 73, front linkage 74, and front rib 75 are colinear in the closed configuration as are the outer edges of rear rib 172, rear linkage 173, front linkage 174, and front rib 175. The rear end of rear linkage 73 rotates relative to the front end of rear rib 72 about location 573; and front end of rear linkage 73 and the rear end of front linkage 74 rotate relative to each other about location 373; and the front end of front linkage 74 rotates relative to the rear end of front rib 75 about location 374. Similarly, the rear end or rear linakge 173 rotates relative to the front end of rear rib 172 about location 673; the front end of rear linkage 173 and the rear end of front linkage 174 rotate relative to each other about location 473; and the front end of front linkage 174 rotates relative to the rear end of front rib 175 about location 474. Sphere 78 is located at its most forward position within the concave internal edges of rear linkages 73 and 173 in this closed configuration of mechanism 70. The purpose of rear ribs 72 and 172 and of front ribs 75 and 175 is to reinforce overall mechanism 70; to guide and prevent unnecessary rotation within the blood vessel of mechanism 70; to allow easy entry into and exit from the blood vessel by mechanism 70; and to provide colinearity to rear linkages 73 and 173 and to front linkages 74 and 174 in the closed configuration of mechanism 70.

FIG. 2A is a partially cross sectional side view of front hollow movable cylindrical section 76 of front multilinkage mechanism 70 in the closed configuration wherein only section 76 is partially cross sectioned. FIG. 2A shows the longitudinal central hole of section 76 including radial surface 176 and front circular surface 177. Also shown are surface 77, linkages 74 and 174, linkages 73 and 173, sphere 78, cable 62, and wire 61. Such longitudinal central hole of section 76 freely accommodates, directs, and guides the anteriormost end of wire 61 during its longitudinal motion. There is simultaneuously provided stability to the motion of section 76 longitudinally. In this closed configuration of mechanism 70, the anteriormost end 161 of wire 61 is adjacent to surface 177. Accordingly, the anteriormost end of wire 61 inserts into and moves freely within such longitudinal central hole of section 76. It is apparent that such longitudinal central hole of section 76 does not extend all the way to the anteriormost end of section 76 and does does penetrate surface 77 as will be hereinafter apparent from FIGS. 3 and 5.

FIG. 3 is a a front view of mechanism 70 in the closed configuration showing surface 77, and front ribs 75 and 175. Also shown is third front rib 275 having a structure associated therewith which is similar to the structures associated with ribs 75 and 175.

FIG. 4 is a side view of mechanism 70 in the open configuration showing flexible wire 61, hollow cable 62 of cable structure 60, section 71, rib 72, location 573, linkage 73, location 373, linkage 74, location 374, rib 75, section 76, surface 77, rib 172, location 673, linkage 173, location 473, linkage 174, location 474, rib 175, and sphere 78. Sphere 78 is fixedly connected to wire 61 by way of brazing, welding, soldering or the like; sphere 78 is in its most rearward position with the rear surface thereof touching the internal edges of rear linkages 73 and 173 and the anterior surface of stationary rear section 71 at location 79; rear linkage 73 has rotated counterclockwise relative to rear rib 72; rear linkage 173 has rotated clockwise relative to rear rib 172; front linkage 74 has rotated clockwise relative to front rib 75; front linkage 174 has rotated counterclockwise relative to front rib 175; and the anteriormost end of wire 61 has freely slid backwards within movable front section 76 which has a small longitudinal central hole therein to accommodate wire 61 and the free motion thereof. Also shown are front linkage 274 and rear linkage 273 being associated with front rib 275 of FIG. 3. A similar explanation as above applies to same. Stationary rear section 72 also includes a small longitudinal central hole to accommodate wire 61 and the free longitudinal motion thereof. Rear linkage 73 includes internal concave edge 773 and rear linkage 173 includes internal concave edge 873 which accommodate sphere 78 when it is in its most anterior position when mechanism 70 is in the closed configuration. In the open configuration of mechanism 70, there is also a net rearward displacement of front linkages 74 and 174, and of movable front section 76. The insertion of the anteriormost end of wire 61 into the longitudinal central hole of movable front section 76 provides a guide for the longitudinal motion of wire 61 and also provides stability and serves as a guide for the longitudinal motion of movable front section 76. The angle in between the linkages and their respective ribs in the open configuration is about 140 degrees.

FIG. 4A is a partially cross sectional side view of front hollow movable cylindrical section 76 of front multilinkage mechanism 70 in the open configuration wherein only section 76 is partially cross sectioned. FIG. 4A shows section 76 including surface 77 and its longitudinal central hole further including radial surface 176 and front circular surface 177. Wire 61 is shown connected to sphere 78. The anteriormost end 161 of wire 61 is shown within the longitudinal central hole of section 76 but in this open configuration of mechanism 70 front end 161 of wire 61 is now displaced rearwardly from its original position in the closed configuration of mechanism 70 a distance equal to the rearward displacement of sphere 78.

FIG. 5 is a front view of mechanism 70 in the open configuration showing rib 75, linkage 74, location 373, rib 175, linkage 174, location 473, rib 275, location 574, linkage 274, location 773, and surface 77. A similar explanation applies to linkage 274 and its associated rib and locations as with respect to linkages 74 and 174.

FIG. 6 is a top view of rear manually operated control mechanism 30 of the present invention showing ring 20, section 31, section 32, member 38, set screw 37, ring 40, location 41, ring 50, location 51, wire 61, section 35, and hollow cable-wire structure combination 60 including cable 62. Also shown is rear expanded portion 233 of member 33, slot 238 of member 38, and front expanded portion 234 of member 33. Member 38 is actuated manually anteriorly and rearwardly relative to member 33 by means of rings 40 and 50 and ring 20 such that wire 61 is similarly moved anteriorly and rearwardly. The rear end of wire 61 is fixedly connected to the front end of member 38. Motion of member 38 rearwardly towards rear section 233 causes mechanism 70 to be in the open configuration whereas motion of member 33 anteriorly toward front section 234 causes mechanism 70 to be in the closed configuration. Upon mechanism 70 being in the closed configuration or the open configuration or any configuration therebetween, set screw 37 is turned to tighten same against member 38. Forward motion of member 38 is limited by concave surfaces 773 and 873 coming into contact with sphere 78 and rear motion of member 38 is limited by sphere 78 coming into contact with surface 79.

FIG. 7 is a side view of mechanism 30 showing ring 20, section 31, section 32, member 33, set screw 37, ring 40, section 35, hollow cable-wire structure combination 60, section 234, member 38, and section 233. Also shown is front face 133 of rear section 233, rear face 138 of member 38, front face 139 of member 38, rear face 134 of section 234, and threaded member 36 of set screw means 37.

FIG. 8 is a bottom view of mechanism 30 showing ring 20, section 31, section 32, member 33, set screw 37, threaded member 36, ring 50 and location 51, ring 40 and location 41, section 35, and hollow cable-wire structure combination 60.

Instrument 10 may be used in conjunction with blood vessels such as arteries or veins; ducts; or other luminal structures. The operation of instrument 10 may include in the open configuration rotation and forward and rear motion of same. Instrument 10 may be made of stainless steel or other suitable material.

While the arrangement according to the present invention has been described in terms of a specific illustrative embodiment, it will be apparent to those skilled in the art that many modifications are possible within the spirit and scope of the disclosed principle.

What is claimed is:

1. A surgical instrument for dilating a blood vessel or the like, said instrument comprising:
    a rear manually operated control mechanism further comprising: a stationary member and a movable member being movable longitudinally relative to said stationary member;
    an intermediate hollow cable-wire structure combination including a hollow cable and a flexible wire running therethrough, the rear end of said cable being connected to the front end of said stationary member and the rear end of said wire being connected to the front end of said movable member, said wire being located and being longitudinally movable within said cable in response to the motion of said movable member;
    and a front multilinkage mechanism further comprising: a rear stationary hollow cylindrical section including a plurality of longitudinal ribs, a longitudinal central hole, and having the front end of said cable being connected to the rear end thereof; a similar plurality of rear linkages being in alignment with said rear ribs, the rear ends of said rear linkages being rotatable relative to the front ends of said rear ribs, and said rear ribs further including internal edges; a similar plurality of front linkages being in alignment with said rear linkages and having their rear ends being rotatable relative to the front ends of said rear linkages; and a front movable cylindrical section including a similar plurality of longitudinal ribs and a longitudinal central hole; said wire being located within the longitudinal central hole of said rear stationary section and being located within the longitudinal central hole of said front movable section; said front multilinkage mechanism also further comprising means being fixedly attached to said wire in between said rear stationary section and said front movable section for applying a force to the internal edges of said rear linkages to cause opening of said front multilinkage mechanism in response to the rearward motion of said wire for dilating said blood vessel.

2. The instrument of claim 1 wherein said movable member includes a longitudinal slot; and said control mechanism further comprises: set screw means being attached to said stationary member through said slot; said set screw means adjustably fixing the location of said movable member relative to said stationary member.

3. The instrument of claim 1 wherein said control mechanism also further comprises a thumb ring being rotatably attached to the rear end of said stationary member and also further comprising first and second finger rings being fixedly connected to said movable member on opposite sides thereof for effecting motion of said movable member relative to said stationary member.

4. The instrument of claim 1 wherein said front ribs each includes a slanted front end and wherein said rear ribs each includes a slanted rear end for allowing easy entry into and exit from said blood vessel in the closed configuration of said multilinkage mechanism.

5. The instrument of claim 1 wherein said rear linkages each includes a concave internal edge for accommodating said force applying means in the closed configuration of said multilinakge mechanism when said rear ribs, rear linkages, front linkages, and front ribs are colinear.

6. The instrument of claim 1 wherein said force applying means is a sphere including a longitudinal central hole therein for accommodating said wire, said wire being connected to said sphere along said sphere longitudinal central hole.

7. The instrument of claim 1 wherein said force applying means causes rotation of each rear linkage relative to said rear stationary section in a first direction and wherein each rear linkage causes rotation of its associated front linkage relative to said front movable section in a second direction, and wherein said rear linkages cause rearward displacement of said front linkages and said front movable section in going from the closed configuration to the open configuration of said multilinkage mechanism.

* * * * *